United States Patent [19]

Fields et al.

[11] Patent Number: 5,445,932
[45] Date of Patent: Aug. 29, 1995

[54] METHOD FOR DETECTION OF A NEW MARKER ASSOCIATED WITH HEPATITIS DELTA VIRUS INFECTION

[75] Inventors: Howard A. Fields, Marietta; Yuri Khudyakov; Michael Favorov, both of Atlanta, all of Ga.

[73] Assignee: The United States of America as represented by the Department of Health and Human Services, Washington, D.C.

[21] Appl. No.: 976,358

[22] Filed: Nov. 17, 1992

[51] Int. Cl.6 ................................ C12Q 1/70
[52] U.S. Cl. ........................ 435/5; 436/820; 530/387.9; 530/389.4
[58] Field of Search .............. 435/5; 436/820; 530/387.9, 389.4

[56] References Cited

U.S. PATENT DOCUMENTS 4,619,896 10/1986 Shattock et al. ................ 435/5

FOREIGN PATENT DOCUMENTS 251575 1/1988 European Pat. Off. .
WO91/06562 5/1991 WIPO .

OTHER PUBLICATIONS

Khudyakov et al., A small open reading frame of the hepatitis delta virus antigenomic RNA encodes a protein that elicits antibodies in some infected patients, Virus Research 27:13–24, 1993.

Khudyakov et al. "Amino acid sequence similarity between the terminal protein of hepatitis B virus and predicted hepatitis delta virus gene protein", FEBS 262(2):345–348 (1990).

Primary Examiner—Esther M. Kepplinger
Assistant Examiner—Donna C. Wortman
Attorney, Agent, or Firm—Foley & Lardner

[57] ABSTRACT

Reagents and methods for the detection of a marker which is associated with severe forms of hepatitis delta virus infection are described. A vaccine comprising immunogenically active HDAg' polypeptides is also described.

7 Claims, 5 Drawing Sheets

FIG. 1(A)

```
           *  G  E  T  G  D  F  H  G  I  Y  S
   E  G  L  D  I  R  G  N  R  G  F  P  W  D  I  L  F
GAGGGGCTGGACATAAGGGGAAACCGGGGATTTCCATGGGATATACTCTT
|
631
```

```
  S  Q  P  I  R  P  F  L  P  R  V  V  D  P  S  E  *           (3)
     P  A  D  P  P  F  S  P  Q  S  C  R  P  Q  *              (2)
CCCAGCCGATCCGCCCTTTTCTCCCCAGAGTTGTCGACCCCAGTGAATAA            (1)
                                                 |
                                                730
```

FIG. 1(B)

```
           *  G  E  T  G  D  F  H  R  I  Y  S
   E  G  L  D  I  R  G  N  R  G  F  P  *
GAGGGGCTGGACATAAGGGGAAACCGGGGATTTCCATGAGATATACTCTT
|
631
```

```
  S  Q  P  I  R  P  F  L  P  R  V  V  D  P  S  E  *           (3)
                                                               (2)
CCCAGCCGATCCGCCCTTTTCTCCCCAGAGTTGTCGACCCCAGTGAATAA            (1)
                                                 |
                                                730
```

FIG. 2(A)

|  |  | REFERENCE |
|---|---|---|
|  | ** * * *** **** *** |  |
|  | WDILFPADPPFSPQSCRPQ | (Makino et al., 1987) |
|  | WDILFPADPPFSPQSCRPQ | (Wang et al., 1987) |
|  | WDILFPADPPFSPQSCRPQ | (Kuo et al., 1988) |
|  | WDILFPADPSSPQSCRPQ | (Saldanha et al., 1990) |
| LARGE | WDLLFPADPSSPQSCRPQ | (Chao et al., 1991) |
| HDAg | WDILFPSDPPFSPQSSRPQ | (Chao et al., 1991) |
| "EXTENSION" | WDILFPVDPPFSPQSSRPQ | (Chao et al., 1991) |
|  | WDILFPSDPPFSPQSCRPQ | (Chao et al., 1991) |
|  | WDILLPADPPFSPQSCRPQ | (Deny et al., 1991) |
|  | WDTLFPADPPFSPQSCRPQ | (Deny et al., 1991) |

FIG. 2(B)

|  |  | REFERENCE |
|---|---|---|
|  | * ***** * * *** |  |
|  | TRDSHGIYSSQPTLPSLPRVVDPSE | (Makino et al., 1987) |
|  | TRDFHGIYSSQPIRPFLPRVVDPSE | (Wang et al., 1987) |
|  | TRDFHGIYSSQPIRPFLPRVVDPSE | (Kuo et al., 1988) |
|  | TRDFHGIYSSQPIRPFLPRVVDPSE | (Deny et al., 1991) |
|  | ARDSHGIYSSQPTLPPLPRVVDPSE | (Saldanha et al., 1990) |
| HDAg' | TGDFRGIYSSHPILPFLPRAVVPSE | (Chao et al., 1991) |
| DOMAIN | PGDFRGIYSSQPILPFLPRVVDPSE | (Chao et al., 1991) |
|  | TGDLHGIYSSQPILPSHPRVVDPSE | (Chao et al., 1991) |
|  | ARDLHGIYSSQSTLPSLPRVVDPSE | (Chao et al., 1991) |
|  | DRDLHGIYSSHPILPFLLRVVDPSE | (Chao et al., 1991) |

FIG. 2(C)

| PEPTIDES | CDLHRIYSSQPIRPFLPRVVDPSE | HF-1 |
|---|---|---|
|  | CDSHGIYSSQPTLPSLPRVVDPSE | HF-2 |

FIG. 3

DESCRIPTION OF SERA ANALYSED FOR ANTI-HDAg' ACTIVITY

| DESCRIPTION | NUMBER OF SAMPLES ANALYSED | SAMPLES WITH ANTI-HDAg' ACTIVITY | |
|---|---|---|---|
| | | NUMBER | % |
| HD chronic | 62 | 8 | 12.9% |
| HD acute | 25 | 1 | 4.0% |
| HB+HD coinf | 7 | 0 | 0.0% |
| HB chronic | 24 | 0 | 0.0% |
| HB acute | 14 | 0 | 0.0% |
| HB reconv | 2 | 0 | 0.0% |
| HC chronic | 4 | 0 | 0.0% |
| HD+HC | 10 | 4 | 40.0% |
| HB+HC | 2 | 0 | 0.0% |
| NANBNC | 7 | 0 | 0.0% |
| DONOR | 5 | 0 | 0.0% |
| TOTAL | 162 | 13 | |
| HD | 104 | 13 | 12.5% |
| OTHERS | 58 | 0 | 0.0% |

NOTE:

HD chronic - sera from patients with chronic hepatitis delta
HD acute    - sera from patients with acute superinfection with HDV
HB+HD coinf- sera from patients with HBV and HDV coinfection
HB chronic - sera from patients with chronic hepatitis B
HB acute    - sera from patients with acute hepatitis B
HB reconv  - sera from reconvalescents of hepatitis B
HC chronic - sera from patients with chronoc hepatitis C
HD+HC       - sera from patients with mixed HBV, HDV and HCV infections
HB+HC       - sera from patients with mixed HBV and HCV infections
DONOR       - sera from healthy donors

FIG. 4

CHARACTERISTICS OF SERA FROM PATIENTS WITH A DIAGNOSIS OF HDV INFECTION CONTAINING ANTIBODY REACTIVE WITH SYNTHETIC PEPTIDES HF-1 AND HF-2

| SERA | MARKERS | | | | | |
|---|---|---|---|---|---|---|
| | HBsAg | anti-HBc IgM | anti-HD IgM | anti-HD IgG | anti-C100.3 IgG+IgM | anti-HDAg' IgG (P/N) |
| CON | + | − | − | + | − | 14.3 |
| 5 | + | − | + | + | w+ | 4.2 |
| 41-I | + | − | − | + | + | 18.2 |
| 39 | + | − | − | + | − | 3.3 |
| 41-E | ND | ND | ND | + | − | 28.5 |
| 44 | + | − | + | + | − | 3.7 |
| 6 | + | − | − | + | w+ | 41.1 |
| 43 | + | − | − | + | − | 97.0 |
| 17 | + | − | + | + | + | 43.8 |
| 3-KN | + | − | − | + | ND | 3.4 |
| 4-N | + | − | + | + | − | 36.9 |
| 7-N | + | − | − | + | ND | 3.6 |
| 8-N | + | − | − | + | ND | 5.2 |

A) Positive to negative (P/N) ratios was determined as described in Materials and Methods;

B) For specimen CON, the N value was derived by utilizing an average OD value obtained by reacting HF-1 and HF-2 directly with human IgG conjugated to horseradish peroxidase containing the following reactivities: anti-HCV, anti-HAV, and anti-HDV (devoid anti-HDAg');

ND - no data, (−) negative, (+) positive, w+ - weak positive.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear     ( x i ) SEQUENCE DESCRIPTION: SEQ ID NO:1:

```
GAGGGGCTGG ACATAAGGGG AAACCGGGGA TTTCCATGGG ATATACTCTT CCCAGCCGAT      60
CCGCCCTTTT CTCCCAGAG TTGTCGACCC CAGTGAATAA                            100
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( D ) TOPOLOGY: linear     ( x i ) SEQUENCE DESCRIPTION: SEQ ID NO:2:

```
Glu Gly Leu Asp Ile Arg Gly Asn Arg Gly Phe Pro Trp Asp Ile Leu
 1               5                  10                  15
Phe Pro Ala Asp Pro Pro Phe Ser Pro Gln Ser Cys Arg Pro Gln
         20                  25                  30
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear     ( x i ) SEQUENCE DESCRIPTION: SEQ ID NO:3:

```
       Gly Glu Thr Gly Asp Phe His Gly Ile Tyr Ser Ser Gln Pro Ile Arg
       1               5                   10                  15

Pro Phe Leu Pro Arg Val Val Asp Pro Ser Glu
                   20                  25
```

( 2 ) INFORMATION FOR SEQ ID NO:4:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear     ( x i ) SEQUENCE DESCRIPTION: SEQ ID NO:4:

```
GAGGGGCTGG ACATAAGGGG AAACCGGGGA TTTCCATGAG ATATACTCTT CCCAGCCGAT          60

CCGCCCTTTT CTCCCCAGAG TTGTCGACCC CAGTGAATAA                              100
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear     ( x i ) SEQUENCE DESCRIPTION: SEQ ID NO:5:

```
       Glu Gly Leu Asp Ile Arg Gly Asn Arg Gly Phe Pro
       1               5                   10
```

( 2 ) INFORMATION FOR SEQ ID NO:6:

( i ) SEQUENCE CHARACTERISTICS:
        ( A ) LENGTH: 27 amino acids
        ( B ) TYPE: amino acid
        ( D ) TOPOLOGY: linear     ( x i ) SEQUENCE DESCRIPTION: SEQ ID NO:6:

```
       Gly Glu Thr Gly Asp Phe His Arg Ile Tyr Ser Ser Gln Pro Ile Arg
       1               5                   10                  15

Pro Phe Leu Pro Arg Val Val Asp Pro Ser Glu
                   20                  25
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:7:

```
       Trp Asp Ile Leu Phe Pro Ala Asp Pro Phe Ser Pro Gln Ser Cys
       1               5                   10                  15

Arg Pro Gln
```

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:8:

```
       Trp Asp Ile Leu Phe Pro Ala Asp Pro Pro Ser Ser Pro Gln Ser Cys
       1               5                   10                  15

Arg Pro Gln
```

( 2 ) INFORMATION FOR SEQ ID NO:9:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:9:

```
Trp Asp Leu Leu Phe Pro Ala Asp Pro Pro Ser Ser Pro Gln Ser Cys
1               5                   10                  15

Arg Pro Gln
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:10:

```
Trp Asp Ile Leu Phe Pro Ser Asp Pro Pro Phe Ser Pro Gln Ser Ser
1               5                   10                  15

Arg Pro Gln
```

( 2 ) INFORMATION FOR SEQ ID NO:11:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:11:

```
Trp Asp Ile Leu Phe Pro Val Asp Pro Pro Phe Ser Pro Gln Ser Ser
1               5                   10                  15

Arg Pro Gln
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:12:

```
Trp Asp Ile Leu Phe Pro Ser Asp Pro Pro Phe Ser Pro Gln Ser Cys
1               5                   10                  15

Arg Pro Gln
```

( 2 ) INFORMATION FOR SEQ ID NO:13:

( i ) SEQUENCE CHARACTERISTICS:
        ( A ) LENGTH: 19 amino acids
        ( B ) TYPE: amino acid
        ( D ) TOPOLOGY: linear     ( x i ) SEQUENCE DESCRIPTION: SEQ ID NO:13:

```
Trp Asp Ile Leu Leu Pro Ala Asp Pro Pro Phe Ser Pro Gln Ser Cys
1               5                   10                  15

Arg Pro Gln
```

( 2 ) INFORMATION FOR SEQ ID NO:14:

( i ) SEQUENCE CHARACTERISTICS:
        ( A ) LENGTH: 19 amino acids
        ( B ) TYPE: amino acid
        ( D ) TOPOLOGY: linear ( x i ) SEQUENCE DESCRIPTION: SEQ ID NO:14:

Trp Asp Thr Leu Phe Pro Ala Asp Pro Pro Phe Ser Pro Gln Ser Cys
1               5                   10                  15
Arg Pro Gln ( 2 ) INFORMATION FOR SEQ ID NO:15:

( i ) SEQUENCE CHARACTERISTICS:
      ( A ) LENGTH: 25 amino acids
      ( B ) TYPE: amino acid
      ( D ) TOPOLOGY: linear    ( x i ) SEQUENCE DESCRIPTION: SEQ ID NO:15:

Thr Arg Asp Ser His Gly Ile Tyr Ser Ser Gln Pro Thr Leu Pro Ser
1               5                   10                  15
Leu Pro Arg Val Val Asp Pro Ser Glu
                20                  25

( 2 ) INFORMATION FOR SEQ ID NO:16:

( i ) SEQUENCE CHARACTERISTICS:
      ( A ) LENGTH: 25 amino acids
      ( B ) TYPE: amino acid
      ( D ) TOPOLOGY: linear    ( x i ) SEQUENCE DESCRIPTION: SEQ ID NO:16:

Thr Arg Asp Phe His Gly Ile Tyr Ser Ser Gln Pro Ile Arg Pro Phe
1               5                   10                  15
Leu Pro Arg Val Val Asp Pro Ser Glu
                20                  25

( 2 ) INFORMATION FOR SEQ ID NO:17:

( i ) SEQUENCE CHARACTERISTICS:
      ( A ) LENGTH: 25 amino acids
      ( B ) TYPE: amino acid
      ( D ) TOPOLOGY: linear    ( x i ) SEQUENCE DESCRIPTION: SEQ ID NO:17:

Ala Arg Asp Ser His Gly Ile Tyr Ser Ser Gln Pro Thr Leu Pro Pro
1               5                   10                  15
Leu Pro Arg Val Val Asp Pro Ser Glu
                20                  25

( 2 ) INFORMATION FOR SEQ ID NO:18:

( i ) SEQUENCE CHARACTERISTICS:
      ( A ) LENGTH: 25 amino acids
      ( B ) TYPE: amino acid
      ( D ) TOPOLOGY: linear    ( x i ) SEQUENCE DESCRIPTION: SEQ ID NO:18:

Thr Gly Asp Phe Arg Gly Ile Tyr Ser Ser His Pro Ile Leu Pro Phe
1               5                   10                  15
Leu Pro Arg Ala Val Val Pro Ser Glu
                20                  25

( 2 ) INFORMATION FOR SEQ ID NO:19:

( i ) SEQUENCE CHARACTERISTICS:
      ( A ) LENGTH: 25 amino acids
      ( D ) TOPOLOGY: linear    ( x i ) SEQUENCE DESCRIPTION: SEQ ID NO:19:

Pro Gly Asp Phe Arg Gly Ile Tyr Ser Ser Gln Pro Ile Leu Pro Phe

```
             1                 5                  10                 15
       Leu  Pro  Arg  Val  Val  Asp  Pro  Ser  Glu
                      20                  25
```

(2) INFORMATION FOR SEQ ID NO:20:

(i) SEQUENCE CHARACTERISTICS:
        (A) LENGTH: 25 amino acids
        (B) TYPE: amino acid
        (D) TOPOLOGY: linear     (xi) SEQUENCE DESCRIPTION: SEQ ID NO:20:

```
       Thr  Gly  Asp  Leu  His  Gly  Ile  Tyr  Ser  Ser  Gln  Pro  Ile  Leu  Pro  Ser
       1                 5                           10                      15
       His  Pro  Arg  Val  Val  Asp  Pro  Ser  Glu
                      20                  25
```

(2) INFORMATION FOR SEQ ID NO:21:

(i) SEQUENCE CHARACTERISTICS:
        (A) LENGTH: 25 amino acids
        (B) TYPE: amino acid
        (D) TOPOLOGY: linear     (xi) SEQUENCE DESCRIPTION: SEQ ID NO:21:

```
       Ala  Arg  Asp  Leu  His  Gly  Ile  Tyr  Ser  Ser  Gln  Ser  Thr  Leu  Pro  Ser
       1                 5                           10                      15
       Leu  Pro  Arg  Val  Val  Asp  Pro  Ser  Glu
                      20                  25
```

(2) INFORMATION FOR SEQ ID NO:22:

(i) SEQUENCE CHARACTERISTICS:
        (A) LENGTH: 25 amino acids
        (B) TYPE: amino acid
        (D) TOPOLOGY: linear     (xi) SEQUENCE DESCRIPTION: SEQ ID NO:22:

```
       Asp  Arg  Asp  Leu  His  Gly  Ile  Tyr  Ser  Ser  His  Pro  Ile  Leu  Pro  Phe
       1                 5                           10                      15
       Leu  Leu  Arg  Val  Val  Asp  Pro  Ser  Glu
                      20                  25
```

(2) INFORMATION FOR SEQ ID NO:23:

(i) SEQUENCE CHARACTERISTICS:
        (A) LENGTH: 24 amino acids
        (B) TYPE: amino acid
        (D) TOPOLOGY: linear     (xi) SEQUENCE DESCRIPTION: SEQ ID NO:23:

```
       Cys  Asp  Leu  His  Arg  Ile  Tyr  Ser  Ser  Gln  Pro  Ile  Arg  Pro  Phe  Leu
       1                 5                      10                      15
       Pro  Arg  Val  Val  Asp  Pro  Ser  Glu
                      20
```

(2) INFORMATION FOR SEQ ID NO:24:

(i) SEQUENCE CHARACTERISTICS:
        (A) LENGTH: 24 amino acids
        (B) TYPE: amino acid
        (D) TOPOLOGY: linear     (xi) SEQUENCE DESCRIPTION: SEQ ID NO:24:

```
       Cys  Asp  Ser  His  Gly  Ile  Tyr  Ser  Ser  Gln  Pro  Thr  Leu  Pro  Ser  Leu
       1                 5                      10                      15
```

-continued

```
Pro Arg Val Val Asp Pro Ser Glu
            20
```

METHOD FOR DETECTION OF A NEW MARKER ASSOCIATED WITH HEPATITIS DELTA VIRUS INFECTION

BACKGROUND OF THE INVENTION

Hepatitis delta virus (HDV) is a viroid-like agent causing severe forms of hepatitis in infected people. It is a naturally occurring satellite of human hepatitis B virus (HBV) and has been shown to be a human pathogen. Rizzetto, M. et al., Proc. Nat'l Acad. Sci. USA 77: 6124–6128 (1980). HDV infection may occur as a coinfection with HBV, and as a superinfection of an HBV carrier. Each type of infection may cause acute or fulminant hepatitis. Superinfection usually causes chronic hepatitis and eventual death due to cirrhosis and liver failure. Approximately 10,000 new HDV infections occur annually in the United States leading to 1,000 hospitalizations and 50 deaths due to fulminant hepatitis. Approximately 70,000 persons are chronic HDV carriers, and an estimated 750–1,000 die annually of chronic liver disease.

Hepatitis delta virions are 36-nm particles with an envelope composed of hepatitis B surface antigen. The internal part of these particles consists of a HDV-specific protein, hepatitis delta antigen ("HDAg"), and a small genomic RNA. Bonino, F., et al., Infect. Immunol. 43:1000–1005 (1986). HDAg found in the sera and liver of infected humans or experimentally infected animals has been shown to be composed of two protein species of between 24 and 30 kDa or a major 26 kDa protein and multiple minor proteins. Bonino, F., et al., J. Virol. 58: 945–50 (1986) and Puig, J., et al., in: Hepadna Viruses (Robinson, W. et al. eds.) Alan R. Liss, N.Y. pp. 579–590 (1987). All of these proteins appear to be related in sequence and are encoded by the large open reading frame (ORF5) of the HDV antigenomic RNA. Makino, S. et al., Nature 329:343–346 (1987) and Wang, E.-S., et al., Nature, 323:508–513 (1986).

European patent application no. 251 575 by Chiron Corporation entitled "Hepatitis Delta Diagnostics and Vaccines, Their Preparation and Use" (published Jan. 7, 1988), discloses the entire genome of the hepatitis delta virus and several open reading frames in both the genomic and complementary strands. One open reading frame, ORF5, encodes two viral polypeptides, p24 and p27. The ORF5 products are considered to be useful in HDV diagnosis and vaccines.

International Patent Application No. PCT/US90/06077 by Lemon, entitled "Immunological Domains Of Hepatitis Delta Virus Antigen" (published May 16, 1991 as World Patent No. 91/06562), discloses the synthesis of 209 overlapping hexapeptides spanning the 214 amino acid residues of the protein HDAg (ORF2 expression product) in order to map its antigenic domains. Domains recognized by antibodies present in serum from human chronic carriers of HDV included residues 2–7, 63–74, 86–91, 94–100, 159–172, 174–195 and 107–207. Also, residues 2–17, 156–184 and 197–211 were synthesized in bulk and were found to possess significant antigenic activity by microtiter ELISA. It was concluded that the entire 214 amino acids of HDAg are expressed during infection in vivo and that the aforementioned peptides would be useful as diagnostic agents and as vaccines.

Khudyakov, et al., "Amino Acid Sequence Similarity Between The Terminal Protein Of Hepatitis B Virus And Predicted Hepatitis Delta Virus Gene Product", FEBS 262(2): 345–348 (March 1990), identifies HDAg' as a new HDV protein. They also propose that HDAg' is encoded by HDAg mRNA, is synthesized by a translation slippage mechanism and may be involved with interfering in Hepatitis B virus replication. FIG. 2, on page 346, presents the genetic organization of the region 631–730 of HDV antigenomic RNA strand. It also shows the sequences for the translation products of the HDAg' open reading frame and indicates probable slippage sites in translation.

Thus far, hepatitis delta virus infection has been diagnosed by the detection of HDAg, or by the detection of antibody to the antigen (anti-HD). But the pathological significance and diagnostic value of HDAg' as a marker has not been determined and such an assessment is needed. The use of HDAg' polypeptides in vaccines against HDV infection has also previously not been investigated.

SUMMARY OF THE INVENTION

The inventors have evaluated the diagnostic potential of HDAg' and have consequently developed a method of diagnosing hepatitis delta virus infection by the detection of HDAg' in biological samples. Moreover, in assessing the pathological significance of HDAg', applicants have discovered that the presence of anti-HDAg' antibodies in biological samples from patients with HDV infection is associated with the more severe forms of the infection. The inventors also have discovered that HDAg' polypeptides can be used as immunogens against hepatitis delta virus infection.

Accordingly, the present invention relates to a method of predicting the development of severe forms of hepatitis delta virus hepatitis, comprising the step of detecting the presence of anti-HDAg' antibody in a biological sample from a patient with an HDV infection.

The present invention further relates to an assay for the detection of anti-HDAg' antibodies in a biological sample comprising the steps of (a) incubating detectably labeled HDAg' with a biological sample suspected of containing anti-HDAg' antibodies and (b) detecting the presence of anti-HDAg' antibodies which bind to the HDAg' antigen.

The present invention is also directed to an assay for the detection of HDAg' polypeptides in a biological sample comprising the steps of (a) incubating detectably labeled anti-HDAg' antibodies with a biological sample suspected of containing HDAg' polypeptides and (b) detecting the presence of HDAg' polypeptides which bind to the anti-HDAg' antibodies.

The present invention still further relates, respectively, to an anti-HDAg' antibody and to a composition for stimulating in a mammal an immune response against hepatitis delta virus infection, comprising (a) an immunogenically effective amount of a HDAg' polypeptide and (b) a pharmaceutically acceptable carrier for said polypeptide.

DETAILED DESCRIPTION OF PREFERRED EMBODIMENTS

The present invention relates to HDAg' and antibodies which recognize HDAg' and processes and products for producing and using such HDAg' and anti-HDAG' antibodies.

More specifically, the present invention relates to an assay for the detection of anti-HDAg' antibodies in a biological sample and to a method of predicting the progression of HDV hepatitis based upon the results of such an assay. In yet another embodiment, the invention relates to the use of HDAg' as an intermediary in the production of antibodies and the use of such antibodies as diagnostic and therapeutic agents. The invention further relates to a vaccine against HDV infection comprising HDAg'.

Figure 1A:
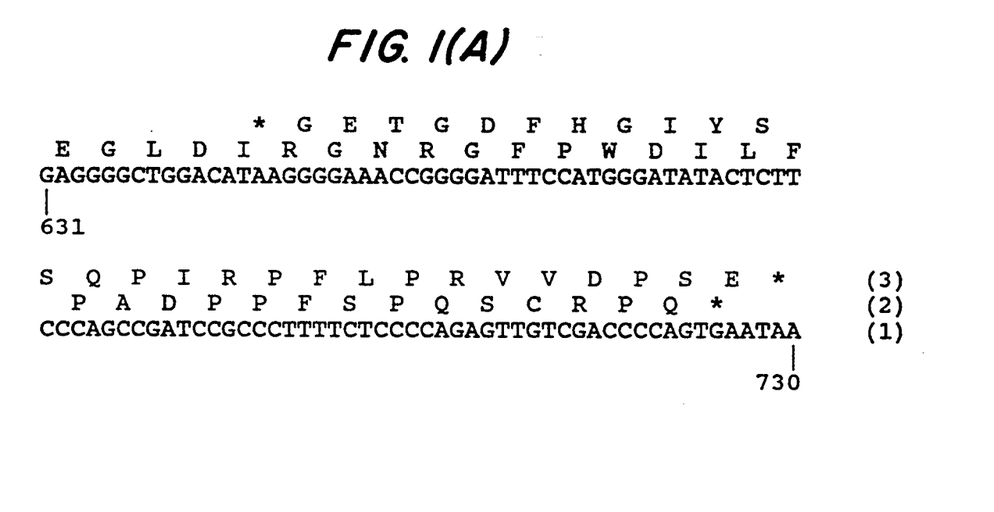
FIGS. 1(A) and (B). Genetic organization of the 3'-terminal region of the open reading frame 5 of the antigenomic RNA encoding for HDAg FIG. 1(A) or small HDAg (B). (1) nucleotide sequence (SEQ ID NOS and 4, respectively) of the region 631–730 of the antigenomic RNA; (2) amino acid sequence (SEQ ID NOS 2 and 5, respectively) in single letter code of the C-terminal region of the large HDAg FIG. 1(A) or the small HDAg FIG. 1(B); asterisk indicates the nonsense codon used to terminate translation of these proteins; (3) amino acid sequence (SEQ ID NOS 3 and 6, respectively) in single letter code of the "HDAg' extension" encoded by the small open reading frame located between two terminator codons indicated by asterisks.
Figure 1B:
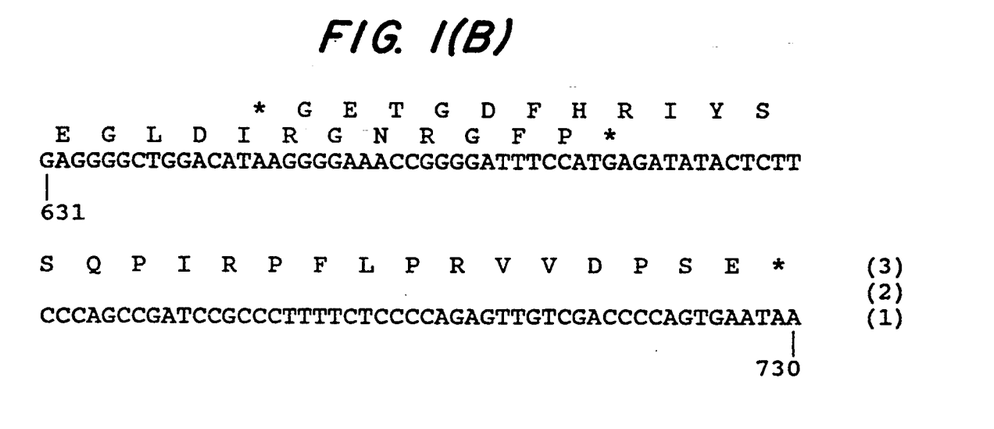
Figure 2A:
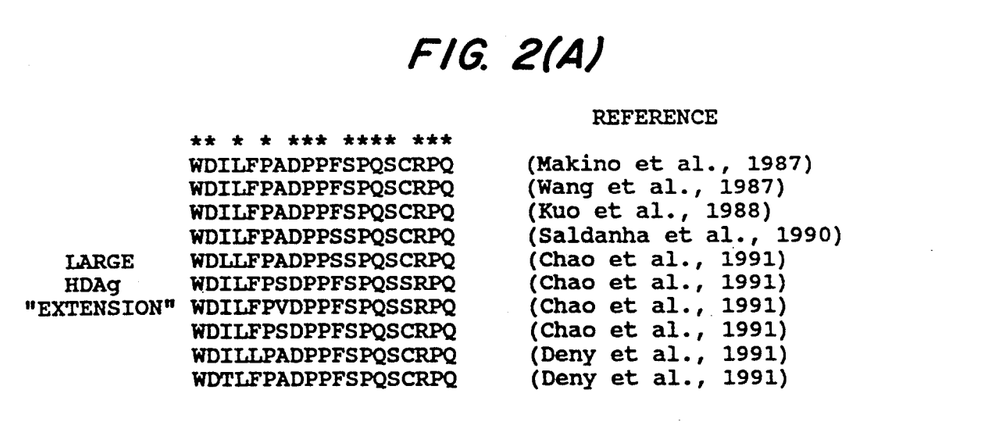
FIGS. 2(A), (B) and (C). Comparison of the "extension sequence" of the large HDAg FIG. 2(A) (SEQ ID NOS 7–14) and HDAg' domain (B) (SEQ ID NOS 15–22) of different HDV isolates. Percent of divergency with consensus is indicated for each sequence. Asterisks show conserved positions.
Figure 2B:
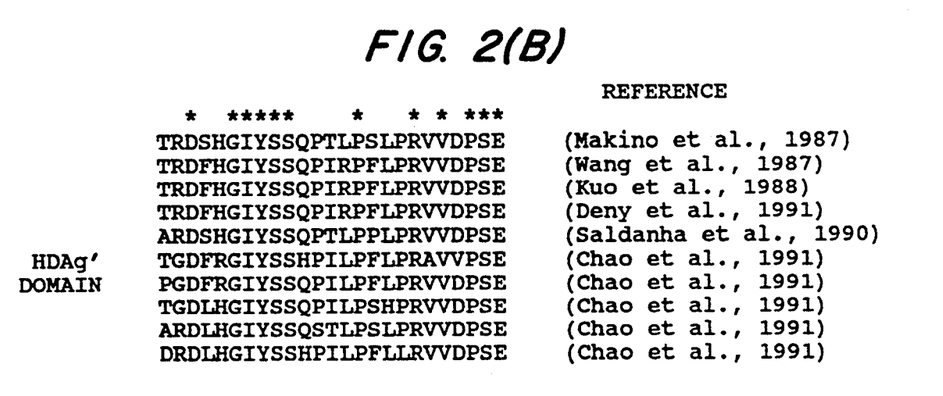
Figure 2C:
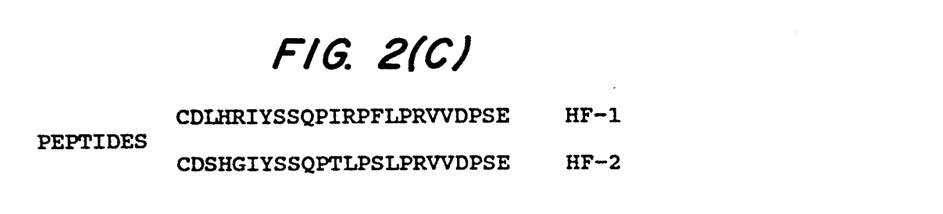
FIG. 2(C)—amino acid sequence of HF-1 and HF-2 peptides (SEQ ID NOS 23 and 24, respectively).

The polypeptide of the present invention comprises a sequence substantially homologous with one of the domains in FIG. 2 (B); more preferably, it is one of the peptides defined in FIG. 2 (C), peptides, HF-1 and HF-2, having the following amino acid sequences SEQ ID NOS 23 and 24, respectively:

HF-1    CDLHRIYSSQPIRPFLPRVVDPSE
HF-2    CDSHGIYSSQPTLPSLPRVVDPSE

The term "polypeptide" or "peptide" in the present context has conventional meaning, i.e., denoting a sequence of amino acids. An amino acid sequence of HDAg' can be modified in accordance with the present invention, for example, by chemical, enzymatic or other treatment which does not diminish the immunogenic activity of the peptide to any extent. The selection of analogues for purposes of the present invention may be based upon the effect of amino acid changes on local hydrophilicity, surface probability, flexibility, antigenic index and secondary structure, as well as on immunoactivity.

An "immunologically active polypeptide" is a polypeptide or fragment thereof which elicits a protective immune response, for example, the production of antibodies against HDAg' in a mammal to which it has been administered.

A "fragment" of a polypeptide according to this invention is a subsequence of HDAg' which is of sufficient size and conformation to remain immunogenically active. That is, a fragment according to the invention comprises at least one epitope of HDAg'.

A polypeptide of the present invention may be in "substantially pure" form, which means that the polypeptide is substantially free from other proteins which would interfere with an in vivo immune response against the polypeptide of the invention.

The polypeptides of the present invention may be synthesized by any conventional manner in the art. For instance, the polypeptides may be synthesized by liquid or solid phase synthesis. In solid phase synthesis, the amino acid sequence of any of the above described polypeptides is constructed by coupling an initial amino acid to a solid support and then sequentially adding the other amino acids in the sequence by peptide bonding until the desired length has been obtained. Merrifield, R. B., J. Am. Chem. Soc., 85:2149 (1963). A preferred method of production involves FMOC-chemistry on an Applied Biosystems automated peptide synthesizer.

The polypeptides of the invention may also be produced by recombinant DNA techniques, such as those set forth generally by Maniatis et al., Molecular Cloning—A Laboratory Manual, Cold Spring Harbor Laboratory (1982). Indeed, the availability of the genomic sequence for HDV permits the construction of expression vectors encoding antigenically active HDAg' or fragments thereof. Fragments encoding HDAg' can be obtained from cDNA clones using conventional restriction digestion or by synthetic methods, and ligated into vectors suitable for any convenient host, according to well known methods in the art. The polypeptides may be prepared by expression of the peptides or of a larger peptide including the desired peptide from a corresponding gene in a suitable host. A fusion peptide may contain a cleavage site whereby the peptide of interest may be released by cleavage of the fused molecule.

The polypeptides of the invention may be coupled to a carrier, according to methods well-known in the art. Immun. Rev. 62:185 (1982). Such carriers include other polypeptides or polysaccharides and may or may not be immunogenic. Preferred carriers include various serum albumins, tetanus toxoids and keyhole limpet hemocyanin. The preferred carrier of the present invention is bovine serum albumin.

The immunogenic polypeptides of the present invention are used to immunize animals and the resulting antisera are useful as diagnostic reagents. The skilled artisan would readily appreciate the fact that lymphocytes or splenocytes from immunized animals may be used to prepare hybridomas capable of secreting monoclonal antibodies directed against epitopes of HDAg' and cross-reactive against the infective virus. Resulting monoclonals are particularly useful for immunodiagnosis of HDV infection, in general, and in the prediction of the progression of HDV hepatitis, in particular. The methods of producing anti-HDAg' polyclonal and monoclonal antibodies are well-known to the art of the invention. Dalchau, et al., Eur. J. Immunol., 10:737–744 (1980).

One embodiment of the present invention relates to an assay for the detection of anti-HDAg' antibodies in a biological sample. As will be apparent to a person skilled in the art, several techniques may be applied in an assay in accordance with the present invention. Thus, preferred embodiments of the invention are based on immunological reactions between antigens and antibodies, detection of the reaction, and correlating the results obtained with results from reference reactions. Preferred assays of the invention are enzyme immunosorbent assays such as enzyme linked immunosorbent assays (ELISA), radioassays (RIA), immunoelectrophoresis assays and the like and involve assaying biological samples from animal subjects.

The ELISA and RIA methods are well established and may be carried out with existing laboratory equipment and may also be subjected to automation. The methods of the invention therefore have wide applicability in clinical laboratories for diagnostic purposes and for monitoring the results of vaccination procedures, and in the pharmaceutical industry as an assay for immunogens to be used in the production of vaccines.

The term "sample" applies to any material to be tested for the presence of anti-HDAg' antibodies or HDAg' polypeptides. The sample may constitute part of a living organism such organ tissue from a mammal, preferably a human. The sample may also be selected from body tissues or body fluids such as blood, blood serum, urine, cerebrospinal fluid, synovial fluid, pericardial fluid, saliva, sputum and body cavity fluid.

The detection and/or quantification of HDAg' or anti-HDAg' antibodies present in a sample may be accomplished in a variety of means known to the skilled artisan. For instance, the assay of the present invention may involve agglutination wherein solid particles to which an HDAg' polypeptide is coupled agglutinates in the presence of anti-HDAg' antibody.

However, it is a matter of routine in the art of immunoassays to include in an assay a detectable label for either the ligand or receptor. A suitable label may be detectable itself or may be reacted with another substance to produce a detectable product. Thus, the label may include radioactive isotopes, enzymes, chromophores, fluorescent or chemiluminescent substances, and complexing agents.

Examples of enzymes useful as labels are β-galactosidase, urease, glucosidases, glucose oxidase, carbonic anhydrase, peroxidases, such as horseradish peroxidase, phosphatases, such as alkaline or acid phosphatase, glucose-6-phosphate dehydrogenase, murinase and ribonuclease. Because enzymes alone are not detectable, they must be combined with a substrate to catalyze a reaction which produces a detectable end product. Thus, a substrate may be added to the reaction mixture resulting in a colored, fluorescent or chemiluminescent product or in a color change or in a change in the intensity of the color, fluorescence or chemiluminescence. Suitable substrates include $H_2O_2$, p-nitrophenylphosphate, lactose, urea, β-D-glucose, $CO_2$, RNA, starch, or malate. The preferred label of the assay of the present invention comprises horseradish peroxidase.

In one embodiment of the present invention, the diagnostic agent is an immunologically active HDAg' polypeptide or fragment thereof which is coupled to a bridging molecule which is coupled to a solid support. The bridging molecule, which is designed to link the solid support and the immunologically active components may be, for example, hydrazide, Protein A, glutaraldehyde, carbodimiide or lysine.

The solid support of the assay of the invention may be a polymer or a matrix coated with a polymer. The matrix may be of any solid material, e.g. glass, paper or plastic. The polymer may be plastic, cellulose, nitrocellulose paper or cyanogenbromide-activated paper. Suitable plastics include latex, a polystyrene, polyvinylchloride, polyurethane, polyacrylamide, polyvinylacetate and any suitable copolymer thereof.

The solid support may be in the form of a tray, a plate such as a microtiter plate, e.g. a thin layer or, preferably, strip, film, threads, solid particles such as beads, including Protein A-coated bacteria, or paper.

In a preferred assay of the invention, the sample is human sera which is added to microtiter wells to which HDAg' peptides have been adsorbed. Anti-HDAg' antibodies which bind to the polypeptides are detected when affinity chromatography purified anti-human antibodies (gamma-chain specific) conjugated to horseradish peroxidase are then added to the microtiter wells. Alternatively, Mμ-chain specific antibodies conjugated to horseradish peroxidase may be used to develop an IgM-specific assay within the scope of the present invention.

In another embodiment, the invention relates to a method of determining the presence of HDAg' in a biological sample, which method comprises incubating the sample with an anti-HDAg' antibody and detecting the presence of the antibody which binds to HDAg' after the incubation. The antibody may be labeled, as described above, or may be bound to a solid support, according to methods well-known in the art of the invention.

In yet another embodiment, the present invention relates to a method of predicting the progression of HDV hepatitis. Indeed, the inventors have discovered that the presence of anti-HDAg' antibody activity is a prognostic marker for the development of severe forms of HDV-associated hepatitis.

Figure 3:
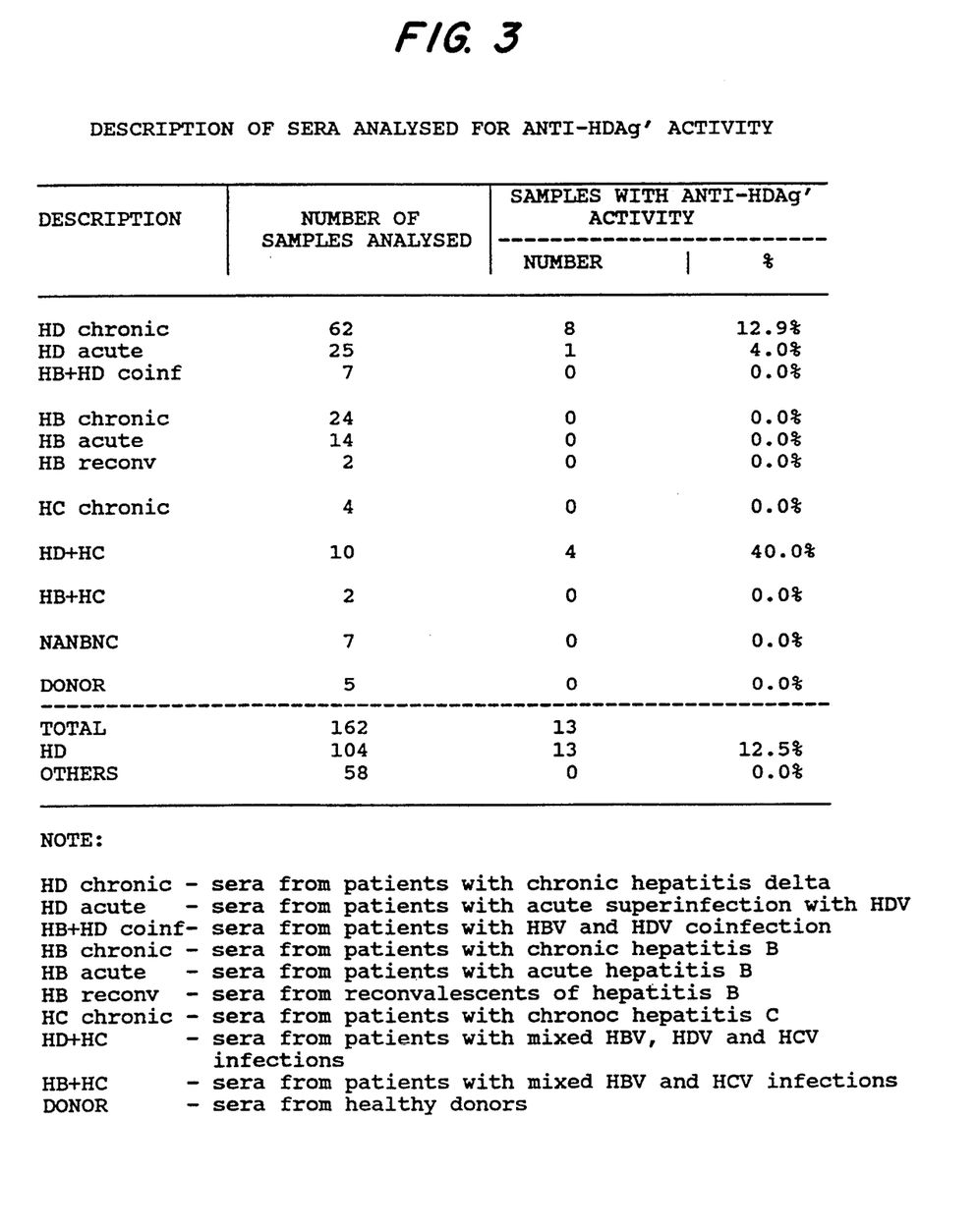
FIG. 3. Enzyme immunoassay analysis using both BSA conjugated and non-conjugated synthetic peptides adsorbed to microtiter plate wells and anti-peptide activity in sera obtained from a HDV infected individuals.
Figure 4:
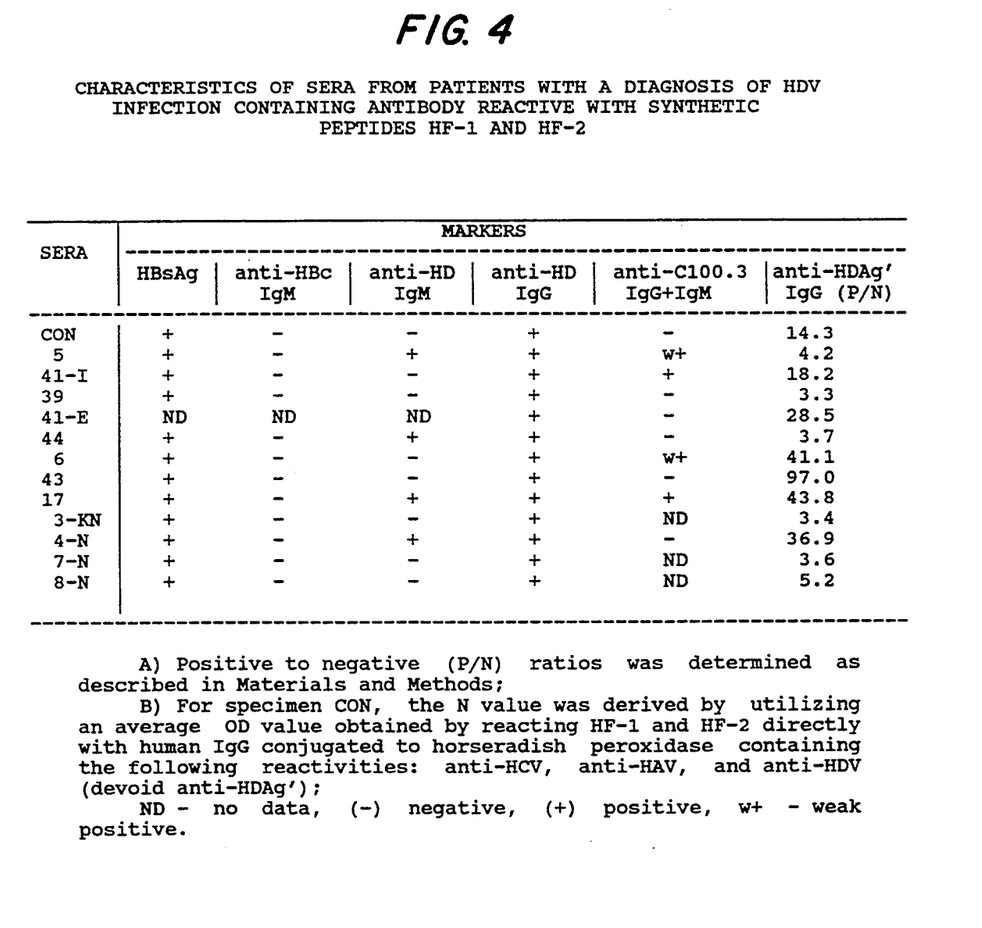
FIG. 4. Characteristics of sera from patients with a diagnosis of HDV infection containing antibody reactive with synthetic peptides HF-1 and HF-2.
Figure 5A:
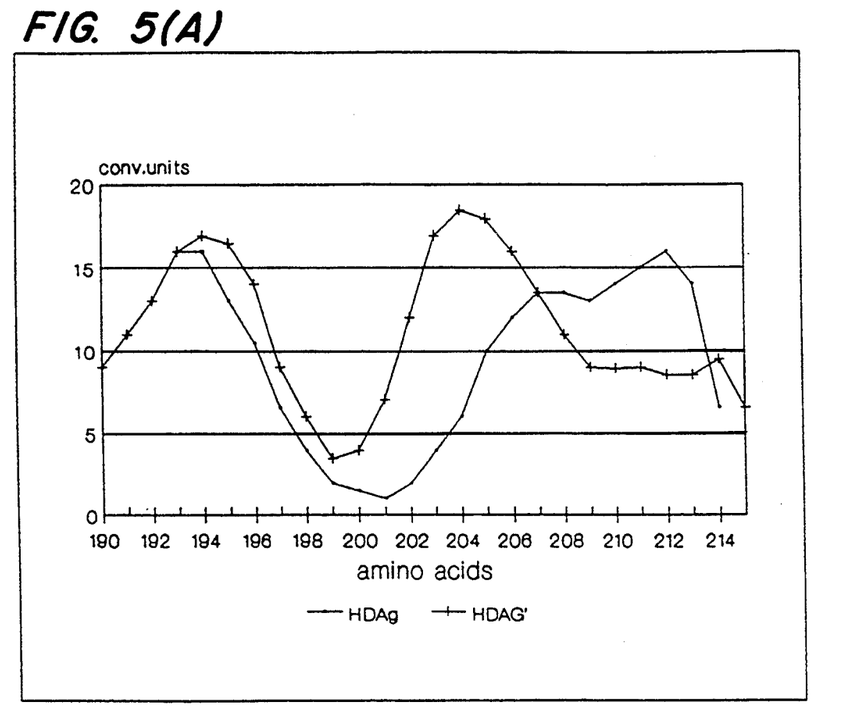
FIG. 5(A). Comparison of the flexibility profiles obtained by the method of Karplus and Schulz, Naturwissenschaften 72:212–213 (1985) for the large HDAg "extension" and for HDAg' domain.
Figure 5B:
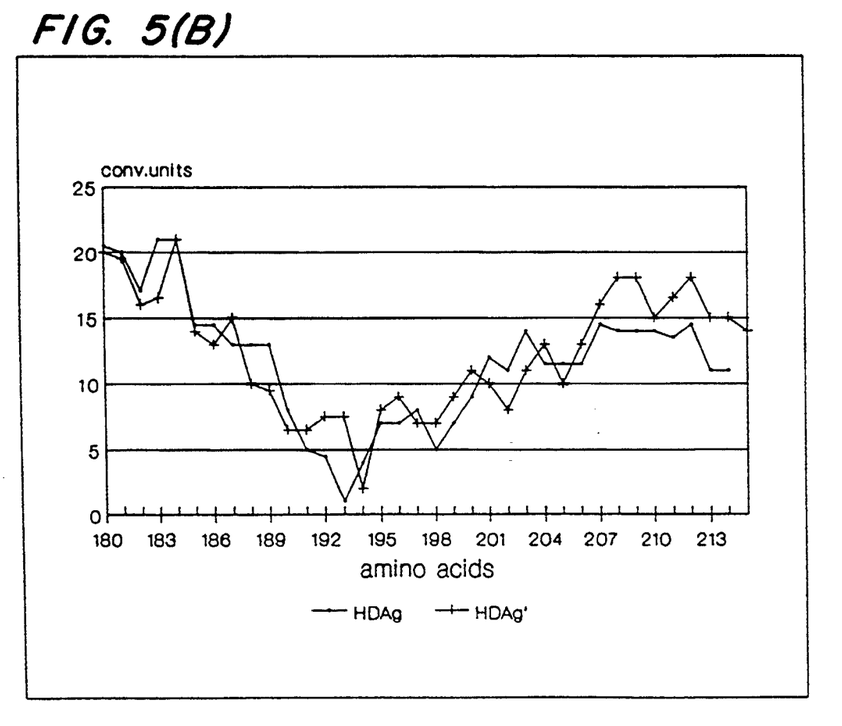
FIG. 5(B). Comparison of the hydropathy plots obtained by the method of Hopp and Woods, Proc. Nat'l Acad. Sci. USA 78:3824–3828 (1981).

Specifically, peptides HF-1 and HF-2, representing the two distinctive forms of HDAg' domains (FIG. 2(C), SEQ ID NOS 23 and 24), were used for the development of an enzyme immunoassay (EIA) for the detection of specific antibodies in sera from HDV infected patients, as described in Example 3, below. EIA analysis using both BSA conjugated and non-conjugated synthetic HDAg' peptides adsorbed to microtiter plate wells and anti-human IgG conjugated to horseradish peroxidase (HRP) as a detectable label demonstrated anti-peptide activity in sera obtained from a HDV infected individuals (FIG. 3). Specificity of the assay was ascertained by testing sera from patients with chronic and acute HBV infection (n=38), resolved HBV infection (n=2), HDV infection (n=94), hepatitis C virus, (HCV) infection (n=4), non-A, non-B, non-C infection (n=7), and healthy donors (n=5). Additionally, the inventors tested samples of sera from patients with mixed infections of HBV and HCV (n=2); or mixed infections of HBV, HDV, and HCV (n=10) (FIG. 3). Anti-peptide activity was not detected in any specimen without markers of HDV infection. By the term "markers of HDV infection" is meant circulating anti-HD antibodies. Amongst HDV-infected patients, 13 were identified as reactive for anti-HDAg' by EIA. Six of these identifications were slightly positive with positive to negative ratio (P/N) equal to 3.3–5.2. Seven sera demonstrated higher levels of reactivity with P/N ratios greater than 14 (FIG. 4). Presence of the anti-HDAg' reactivity was found only in sera from patients infected with HDV. Among HBV-infected patients without any evidence of HDV infection (n=42), anti-HDAg' was not observed. This observation was statistically significant (P=0.02).

In order to confirm specificity, experiments were conducted by blocking the antibody from binding to the synthetic peptide fixed on the solid phase. The inventors developed a neutralization test using either synthetic peptides alone or peptides conjugated to BSA as blocking reagents. They used sera positive and negative for anti-HDAg' activity and, in addition to HF-1 and HF-2 synthetic peptides, used a synthetic peptide corresponding to the region 169–179 of HDAg as a control in the blocking experiments. The inventors observed no blocking effect with peptide 169–179. However, incubation of the HF-1 or HF-2 peptides with specimens, containing antibodies to HDAg' drastically decreased the capture of the antibodies by the synthetic peptide adsorbed to the surface of the microtiter well and had no effect on background reactivity with negative sera. Reactivity with peptides adsorbed to the solid phase decreased 2 to 5 times for sera Nos. 5 and 41I, 5–10 times for sera Nos. 6 and 43, more than 45 times for serum No. 44, and 15–25 times for others (FIG. 4).

Additionally, the inventors developed another confirmatory test to ascertain specificity. That is, they prepared an IgG fraction from serum CON (FIG. 4). This conjugate reacted with the synthetic peptides that were adsorbed to microtiter wells. This reaction was specifically inhibited by 50–80% with all sera reactive to synthetic peptides and not by any other sera tested.

Both synthetic peptides HF1 and HF2 interact with antibodies from the same sera. Peptide HF-1, however, is usually more reactive than peptide HF-2. This difference may be due to different adsorptive characteristics of the peptides to the solid phase. Another possible explanation may be due to a difference in the immunogenicity of the two domains.

Antibody reactive with synthetic peptides HF-1 and HF-2 were found more frequently in sera from patients with chronic disease than with acute HDV infection (FIG. 3). All eight cases of chronic HDV infection with anti-HDAg' activity also had severe forms of hepatitis. Four of ten sera from patients each containing markers of HBV, HCV, and HDV infection also demonstrated antibody reactivity with synthetic peptides HF-1 and HF-2 (FIG. 3). Among the few cases of HDV-HCV mixed infections, 40% of the sera contained antibody to HDAg'. Because a high percentage of the patient population who tested positive for anti-HDAg' also have died, these results indicate that the presence of anti-HDAg' activity is a prognostic marker for the development of severe forms of HDV-associated hepatitis. By "severe forms of HDV-associated hepatitis" is meant that the infection results in a shortened life-span. It is well-understood to the skilled artisan that a "higher percentage of deaths" is a relative term which refers to the situation where more deaths occur in groups of individuals who have anti-HDAg' than in groups who do not have anti-HDAg'.

Another embodiment of the present invention relates to a vaccine comprising HDAg' polypeptides or fragments thereof. The vaccine may comprise at least one HDAg' polypeptide combined with other HDV antigens.

The preparation of vaccines which contain peptide sequences as active ingredients is well understood in the art. Typically, such vaccines are prepared as injectables, either as liquid solutions or suspensions; solid forms suitable for solution in, or suspension in, liquid prior to injection may also be prepared. The preparation may also be emulsified or the protein encapsulated in liposomes. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkaline glycols or triglycerides; such suppositories may be formed from mixtures containing the active ingredient in the range of 0.5% to 10%, preferably 1%–2%. Oral formulations include well-known excipients such as pharmaceutical grades of mannitol, lactose, starch magnesium stearate, sodium saccharine cellulose, magnesium carbonate and the like. These compositions take the form of solutions, suspensions, tablets, pills, capsules, sustained release formulations or powders and contain 10%–95% of active ingredient, preferably 25%–70%.

The polypeptides may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases.

The vaccine of the present invention may be administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of the active ingredient required to be administered depends on the judgment of the skilled practitioner with knowledge of the specific requirements of the subjects to be treated.

The invention will be further described with respect to the following examples; however, the scope of the invention is not to be limited thereby.

EXAMPLE 1

Peptide Synthesis

Peptides HF-1 and HF-2, the amino acid sequence for which are in FIG. 2(C) (SEQ ID NOS 23 and 24), were synthesized by FMOC-chemistry on Applied Biosystems automated peptide synthesizer model 430-A. The synthetic peptides were coupled to bovine serum albumin (BSA) using m-maleimidobenzoic acid N-hydroxysuccinimide ester (MBS) as a coupling agent (Aldrich Chemical Company, Inc., Wisconsin, USA).

EXAMPLE 2

Sera

All samples of sera were selected from the collection reposited at the D.I. Ivanovsky Institute of Virology, Moscow. Each serum sample was obtained from an individual patient. Sera from HDV infected patients with chronic hepatitis B were tested for the presence of HBsAg, and IgG and/or IgM anti-HD. Sera were also selected from hepatitis patients with anti-C100.3 activity, a marker of hepatitis C virus (HCV) infection, or from individuals without markers of hepatitis A, B, C, or D.

EXAMPLE 3

Enzyme Immunoassay

Microtiter wells (Immulon 1, Dynatech Laboratories, Inc.) were adsorbed with 100 μl BSA-conjugated or unconjugated synthetic peptides at a concentration of 5 μg per well. Human sera were diluted 1:20 in 0.1M PBS, pH7.5, containing 0.1% Tween 20 (a non-ionic detergent) and 5% normal goat serum, and 100 μl were added to each well to capture antibodies reactive to the adsorbed peptides. To identify sera and isotype containing anti-peptide activity, affinity purified anti-human antibodies conjugated to horseradish peroxidase (HRP) (heavy-chain specific, TAGO, Inc., Burlingame, Calif., USA) were used. The cutoff, expressed as a P:N ratio, was statistically established equal to 3.0, where the P represents the OD value at 490 nm of the experimental specimen and N represents the OD value of negative controls. Typically, the OD value for negative controls was $0.02 +/- 0.002$.

The inventors have conducted two tests to confirm specificity. The first test involved blocking the antibody from binding to the synthetic peptide fixed on the solid phase with synthetic peptides. Briefly, the serum, appropriately diluted, was incubated for 1 hour at 37° C. with 5-10 μg of synthetic peptide unconjugated or conjugated to BSA. The second test involved blocking the antibody from binding to the synthetic peptides with a serum specimen. A HRP conjugate was prepared from the IgG fraction obtained from the specimen labeled CON (FIG. 4). This IgG:HRP conjugate was prepared by the method of Nakane and Kawaoi, J. Histochem., 22:1084-1091 (1974) and was reactive with both synthetic peptides adsorbed to the surface of microtiter plate wells at a dilution of 1:1000. To demonstrate specificity of the conjugate and other sera reactive with these synthetic peptides, the HRP-conjugate was diluted 1:1000 and mixed with a 1:10 dilution of test specimens and incubated for 1 hour at 37° C. in the microtiter wells containing adsorbed peptides HF-1 or HF-2. Each initially reactive specimen for anti-HDAg' activity and some negative sera were analyzed by this competition experiment.

---

What is claimed is:

1. A method of predicting the clinical outcome of hepatitis delta virus (HDV) hepatitis, comprising detecting the presence of anti-HDAg' antibodies in a biological sample from a patient having HDV infection, wherein the presence of anti-HDAg' antibodies predicts a shortened lifespan in said patient.

2. An assay for the detection of anti-HDAg' antibodies in a biological sample comprising the steps of:
   (a) incubating detectably labeled HDAg' polypeptide with a biological sample suspected of containing anti-HDAg' antibodies; and
   (b) detecting the presence of anti-HDAg' antibodies which bind to said HDAg' polypeptide.

3. The assay of claim 2, wherein said biological sample is selected from the group consisting of blood, blood serum, urine, cerebrospinal fluid, synovial fluid, pericardial fluid, saliva, sputum, and body cavity fluid.

4. The assay of claim 3, wherein said HDAg' polypeptide is either HF-1 or HF-2.

5. An assay for the detection of HDAg' polypeptides in a biological sample comprising the steps of:
   (a) incubating detectably labeled anti-HDAg' antibodies with a biological sample suspected of containing HDAg' polypeptides;
   (B) detecting the presence of HDAg' polypeptides which bind to said anti-HDAg' antibodies.

6. The assay of claim 5, wherein said biological sample is selected from the group consisting of blood, blood serum, urine, cerebrospinal fluid, synovial fluid, pericardial fluid, saliva, sputum, and body cavity fluid.

7. An isolated and purified anti-HDAg' antibody.

* * * * *